United States Patent [19]

Wilkerson

[11] Patent Number: 4,590,932
[45] Date of Patent: May 27, 1986

[54] ANKLE-SPRAIN EDEMA-CONTROL BOOT ASSEMBLY

[76] Inventor: Gary B. Wilkerson, 406 Perkins Ave., Danville, Ky. 40422

[21] Appl. No.: 610,269

[22] Filed: May 14, 1984

[51] Int. Cl.$^4$ .............................................. A61F 13/06
[52] U.S. Cl. .................................. 128/166; 128/80 H
[58] Field of Search ..................... 128/166, 80 H, 165, 128/166.5, 157, DIG. 15, 89 R, 90

[56] References Cited

U.S. PATENT DOCUMENTS

| | | | |
|---|---|---|---|
| 332,728 | 12/1885 | McEwen | 128/166 |
| 3,490,450 | 1/1970 | Gardner | 128/DIG. 15 X |
| 3,819,796 | 6/1974 | Webster et al. | 128/90 X |
| 4,133,311 | 1/1979 | Karczewski | 128/80 H X |
| 4,280,489 | 7/1981 | Johnson, Jr. | 128/80 H |
| 4,409,976 | 10/1983 | Pence | 128/166 |
| 4,527,556 | 7/1985 | Nelson | 128/166 X |

OTHER PUBLICATIONS

The Physician and Sports Medicine, vol. 10, No. 8, Aug. 1982, "Controlling Ankle Edema With Pads", Gary B. Wilkerson, p. 195.

*Primary Examiner*—Mickey Yu
*Attorney, Agent, or Firm*—Charles J. Brown

[57] ABSTRACT

A boot assembly applicable to either the left or right ankle and foot to apply compression for controlling edema from either an inversion or an eversion sprain characterized by a reversible (left or right) and eversible (inside or out) pliable boot element with upper and lower flaps oppositely overlapping in a selected left-to-right or right-to-left direction.

12 Claims, 12 Drawing Figures

ANKLE-SPRAIN EDEMA-CONTROL BOOT ASSEMBLY

BACKGROUND OF THE INVENTION

Ankle sprains often cause substantial disability, particularly for athletic activity, and a considerable body of literature has been developed on the more effective methods and means of treatment. Application of cold and compression as soon as possible after the injury are recognized to be of great importance in minimizing edema, which is the accumulation of fluid in the tissue spaces of the ankle. Depending upon the severity of the sprain, blood vessels may be ruptured around the injury site and fluid engorges the spaces between cells causing pain, restriction of joint motion, tissue adhesions, inhibited re-absorption of fluid, possible scar tissue formation and even tissue hardening from thickened edema. It is the purpose of the present invention to provide apparatus by which a selected degree of optimum compression can be applied to the area of the trauma commencing promptly after the injury so as to prevent or if need be reverse accumulation of fluid, but at the same time permit the patient to adjust the apparatus and vary the compression without removing it from the foot and ankle or interrupting compression. Proper circulation and comfort are thereby insured during recovery. The adjustable feature is important because the compression should be relieved from time to time for the patient's comfort, for example during sleeping hours, but never stopped entirely or otherwise the edema will return.

Probably the most relevant prior art is an article which I authored and which was published in a journal entitled *Physician and Sports Medicine*, Volume 10, Number 8, August 1982 (a McGraw-Hill publication). It describes a basic concept of edema-control apparatus for ankle sprains which has been improved in accordance with the present invention. The apparatus of the article concerns a U-shaped compression pad adapted to fit around the malleolus, with legs of the pad extending upwardly and enclosure means disposable around the pad and the ankle and foot to apply compression. Both the enclosure means and the pad referred to in that article have been improved in structure in accordance with my invention claimed herein to achieve more effective results from two general standpoints. The first is that a boot assembly is provided which is reversible (left or right) and eversible (inside or out) so that it can be applied to either the left or right ankle and foot for either inversion or eversion sprains, thereby applying compression firmly but resiliently to those portions of the ankle where it is needed most to prevent or reverse swelling with the least discomfort to the patient. The second advantage is that the apparatus is designed to be adjustable by the patient to vary the extent of compression but without interrupting it, which is to say the apparatus is to remain in place on the ankle and foot twenty-four hours a day during the healing process but is to be easily manipulated to change the degree of compression

SUMMARY OF THE INVENTION

In accordance with the invention a boot assembly is provided which is applicable to either the left or right ankle and foot for applying compression to control edema from either an inversion or an eversion sprain. The assembly comprises a pliable fabric boot element disposable around the ankle and foot from behind. The boot element includes upper and lower flaps on one side and upper and lower flaps on the other side of the front of the boot element. One of the upper flaps is an inner flap disposable against the ankle and the other of the upper flaps is an outer flap adapted to overlap and be secured to the upper inner flap. The lower flap on the same side as the upper outer flap is an inner flap disposable against the foot and the other of the lower flaps is an outer flap adapted to overlap and be secured to the lower inner flap in a direction opposite the overlap of the upper outer flap. By this construction the boot element is reversible and eversible to fit either ankle and foot with a selected right-to-left or left-to-right direction of overlap of the flaps. The assembly also includes pad means adapted to be compressed around the malleolus within the boot element.

Within the definition of the invention recited above, the sub-combination of the improved pad or the aforementioned improved boot element, each independent of the other, is also contemplated.

DESCRIPTION OF THE PREFERRED EMBODIMENT

The malleolus is the protrusion on each side of the ankle, the lateral malleolus of the fibula being on the outside and the medial malleolus of the tibia being on the inside. By far the greatest incidence of ankle sprains are of the so-called inversion type wherein the foot turns inwardly and the area around the lateral malleolus of the fibula is subjected to the greatest edema. A less common form wherein the ankle turns outwardly is known as an eversion sprain. The more common inversion sprain is used as an example in this description though it will be clear that the apparatus is applicable to either type of sprain. In any event it is of great importance to apply compression, together with ice and elevation of the foot, as soon after the injury as is practicable. The object is to prevent fluid from accumulating to a substantial degree in the area of trauma and to reverse whatever initial accumulation has occurred. Swelling typically occurs from the base of the toes up and including the lower portion of the ankle and is especially pronounced in the region of the malleolus.

Figure 1:
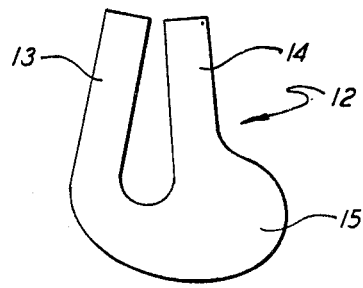
FIG. 1 is an elevation of the pad of the boot assembly shown in its flat form prior to being conformed to the patient's ankle.
Figure 2:
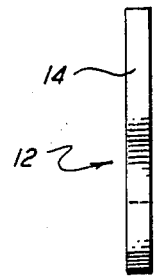
FIG. 2 is an end elevation of the pad of FIG. 1.
Figure 3:
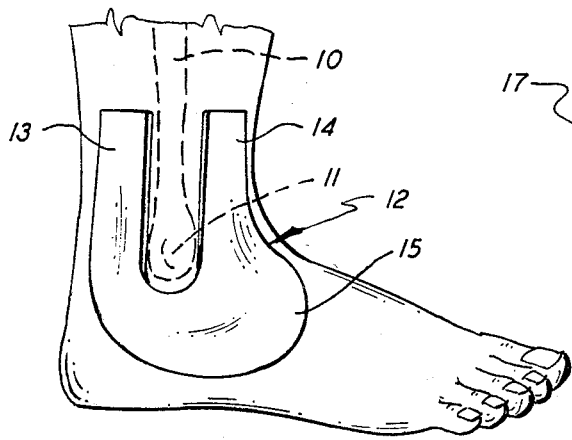
FIG. 3 is a somewhat schematic illustration of the right side of the patient's right foot and ankle showing the pad of FIG. 1 in place around the lateral fibular malleolus and conforming to the contours of the ankle.

Referring now to FIGS. 1 to 4, the right foot of a patient is shown with the fibula 10 and its lateral malleolus 11 illustrated in dotted lines. A pad 12 is provided in accordance with the invention which is of self-supporting thermoplastic foam material. The pad 12 is a substantially U-shaped configuration with legs 13 and 14 and a lower portion 15. Lying flat after being cut or stamped from a sheet of the foam material, the legs 13 and 14 are to be of non-parallel orientation as shown in FIG. 1. If the outer ends of the legs are closer in the flat form of the pad, it has been discovered that the legs automatically spread apart to a substantially parallel position as shown in FIG. 3 when the pad 12 is applied about the malleolus 11 of the patient. It is important to provide an upwardly open channel for release of edema in that direction during the use of the pad 12.

The thermoplastic material of the pad 12 is selected such that by placing the pad in an oven for a brief period and then applying it while warm to the patient's ankle it re-sets to conform to the particular shape of the ankle and foot and insures an equal application of compression to the injured area. The purpose of the lower portion 15 of the pad 12 is to apply compression to the upper area of the patient's foot as well as the area immediately around the malleolus.

Figure 4:
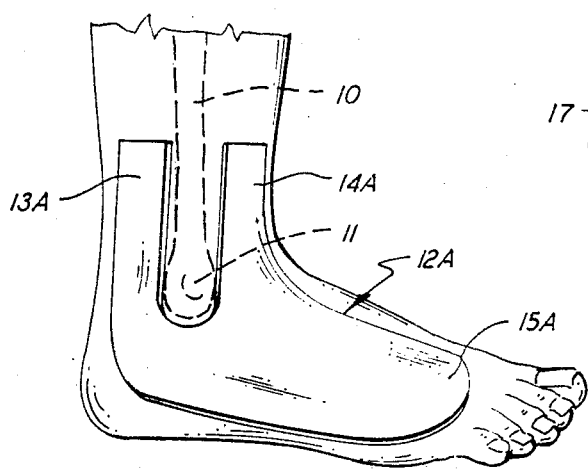
FIG. 4 is a view similar to FIG. 3 showing a form of compression pad designed for more severe sprains.

Another form of pad 12A is illustrated in FIG. 4 which includes upwardly extending legs 13A and 14A similar to those of the pad 12 shown in FIGS. 1 to 3. However the lower portion 15A is of extended length so as to cover a greater area of the patient's foot and thereby control the edema which develops from more severe sprains.

Figure 5:
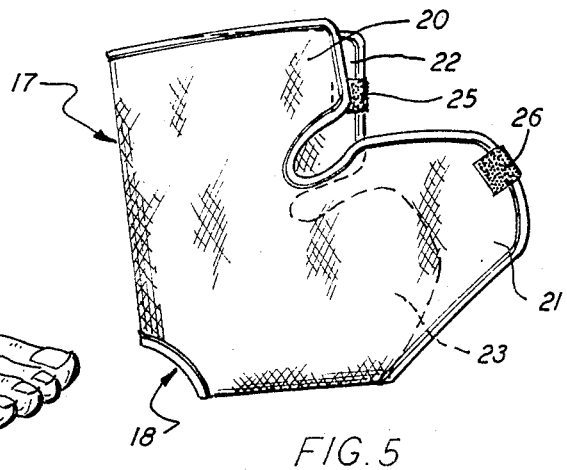
FIG. 5 is an elevation of the pliable boot element of the invention lying flat and in that condition of eversion for use in a right foot inversion ankle sprain or a left foot eversion ankle sprain.
Figure 6:
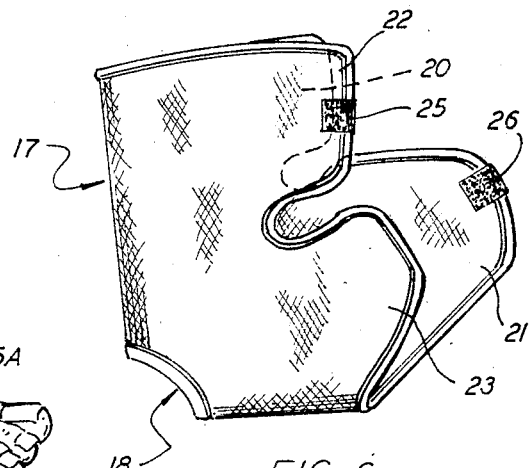
FIG. 6 is an elevation of the same pliable boot element of the invention lying flat but in that condition of eversion for use in a right foot eversion ankle sprain or a left foot inversion ankle sprain.

The boot assembly of the invention also includes a pliable fabric boot element 17 shown in FIGS. 5 and 6 of soft material, one form of which is sold under the trademark "Fastwrap". Its edges are bound with a soft fabric and it has an opening 18 at the rear thereof which will fit around the heel of the patient. An important characteristic of the boot element 17 is that it has substantially identical inner and outer surfaces. When it is turned inside-out, which is to say everted, it presents the same identical soft surface area to the patient's skin.

Upper and lower flaps 20 and 21 are arranged on one side of the boot element, the lower flap 21 being substantially longer than the upper flap 20. Upper and lower flaps 22 and 23 are provided on the other side of the boot element, and again the lower flap 23 is longer than the upper flap 22. Also, the upper flap 22 is somewhat longer than the upper flat 20 and the lower flap 21 is somewhat longer than the lower flap 23. The upper flap 20 is at all times an inner flap to be disposed against the ankle of the patient, and the upper flap 22 is an outer flap which is adapted to overlap and be secured to the upper inner flap 20. The lower flap 23 on the same side as the upper outer flap 22 is an inner flap and is disposable against the foot of the patient. The other lower flap 21 is an outer flap adapted to overlap and be secured to the lower inner flap 23 in a direction opposite the overlap of the upper outer flap 22.

A patch 25 of quick-release hook-and-pile fastener means, such as that sold under the trademark "Velcro", is applied to the upper outer flap 22 and is folded over its edge so that it presents a securing surface on either side thereof. In similar fashion a patch of quick-release hook-and-pile fastener means 26 is folded over the edge of the lower outer flap 21 to present a securing surface on either side thereof.

The boot element 17 is the same in FIGS. 5 and 6 but it is shown in its two everted, which is to say turned inside-and-out, conditions. In FIG. 5 it is shown as it is to be applied as illstrated in FIG. 7 to the right foot of a patient for purposes of treating an inversion sprain. The FIG. 5 everted condition of the boot element 17 would also be used for application to a patient's left foot to treat an eversion sprain. The FIG. 6 condition would be used for a right foot eversion sprain or a left foot inversion sprain. From the foregoing description it will be clear that the boot element 17 is completely reversible and eversible to fit either ankle and foot with a selected right-to-left or left-to-right direction of overlap of the flaps.

Figure 7:
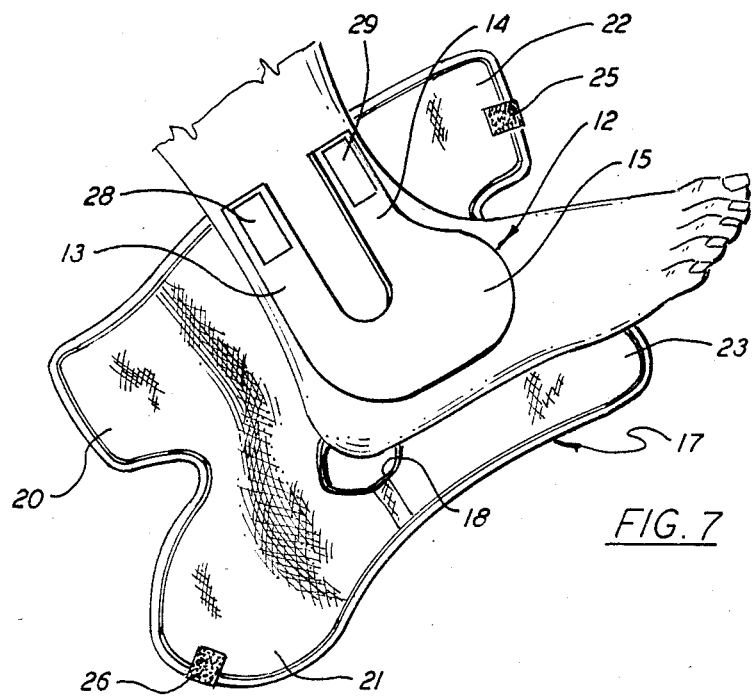
FIG. 7 illustates the boot element of the FIG. 5 eversion condition being initially applied about the pad and the patient's right ankle and foot for an inversion sprain.

FIG. 7 illustrates the first steps in applying the boot assembly to the patient's ankle and foot. Two hook-and-pile patches 28 and 29 are applied to the upper legs 13 and 14 of the pad 12 on the outside of the pad. The patches 28 and 29 may have adhesive on their underside, covered until use by a removable film, so that they may be easily attached to the pad. Their hook surface faces outwardly.

While the pad 12 is held in place by hand, the boot element 17 is applied around the foot from behind with a sole portion underlying the patient's foot as shown in FIG. 7 and the lower inner flap 23 is wrapped across the top of the foot from left-to-right as viewed by the patient. The lower outer flap 21 is then wrapped from right-to-left as viewed by the patient over the lower inner flap 23. The patch 26 secures the outer lower flap 21 in place. The top of the foot generally, from the base of the toes back to the ankle, is thereby compressed by the lower flaps with a squeezing action opposed by the boot element sole portion.

Figure 8:
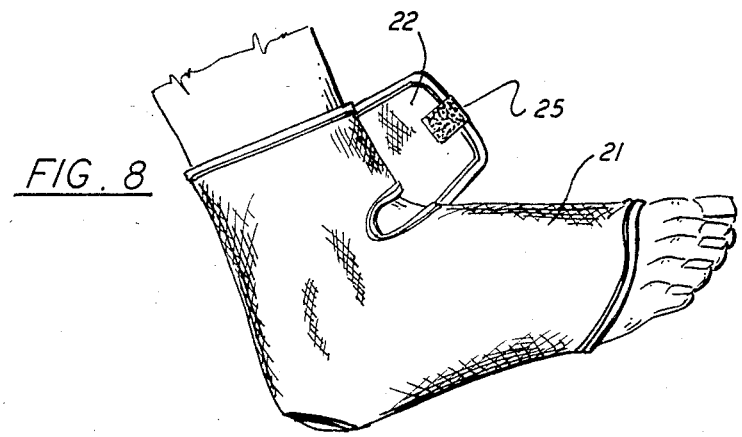
FIG. 8 illustrates the boot element with its lower flaps secured and its upper flaps about to be secured.
Figure 10:
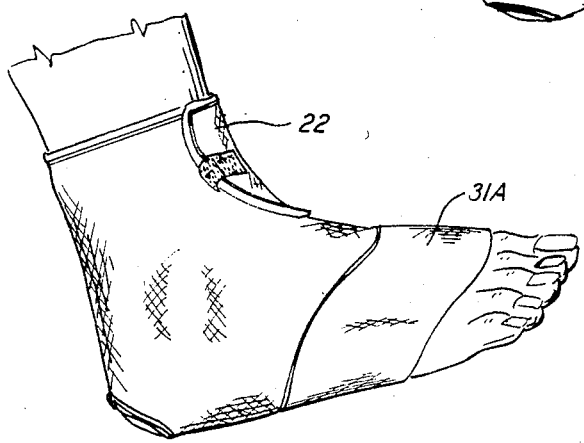
FIG. 10 illustrates the boot element with both flaps secured and the toe foot strap applied.

The upper inner flap 20 is then wrapped from right-to-left as viewed by the patient against the patches 28 and 29 of the pad 12. Next the upper outer flap 22 is applied from left-to-right as viewed by the patient and is secured as shown in FIGS. 8 and 10 by means of the patch 25. It has been found that this left-to-right wrapping direction of the upper flaps and right-to-left wrapping direction of the lower flaps is more suitable for a right foot inversion sprain. It will be understood that by everting the boot element 17, the direction of wrapping will be just the opposite, which is to say from right-to-left of the outer upper flap and from left-to-right of the outer lower flap.

Figure 9:
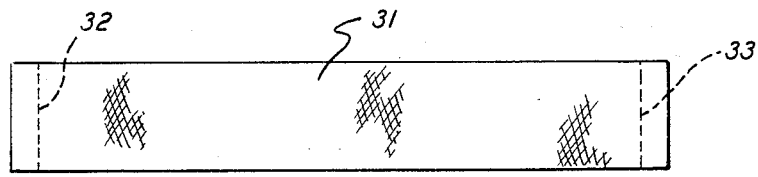
FIG. 9 is a plan view of one of the identical toe and ankle straps of the invention.

Referring to FIG. 9 an elastic strap 31 is shown. It may be of the soft stretchable material used as elastic wrap by athletes for knee and ankle support. On the same side thereof and at opposite ends are hook-and-pile patches 32 and 33 for purposes of securing the strap 31 in place.

One strap of the FIG. 9 form is first applied to the boot element at the base of the patient's toes as shown in FIG. 10. In the assembly shown, it is wrapped from right-to-left as viewed by the patient across the top of the foot. The first applied patch 33 attaches to the outer surface of the fabric boot element and the second applied patch 32 is secured in overlapping relation to the strap 31 itself. This toe strap is illustrated as 31A in FIGS. 10, 12 and 13.

Figure 11:
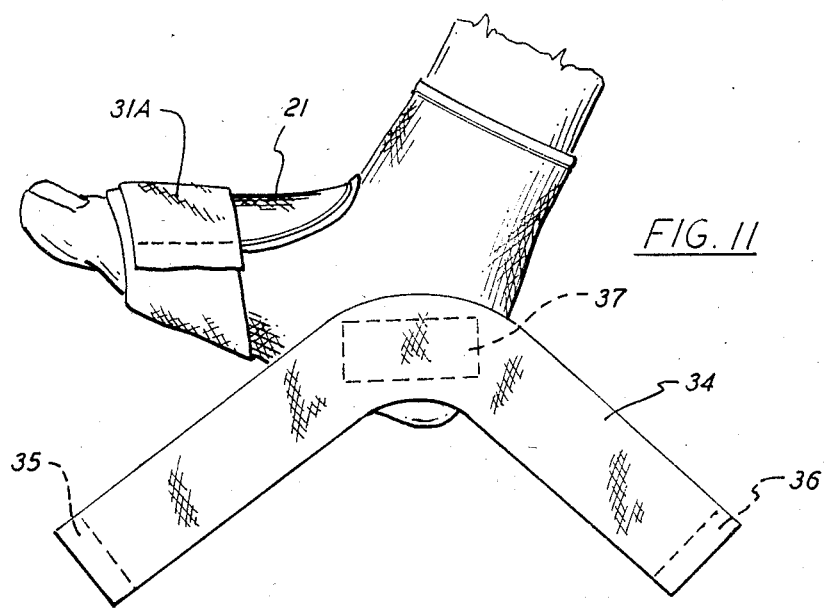
FIG. 11 illustrates the patient's ankle and foot from the left side and showing the initial positioning of the intermediate strap.
Figure 12:
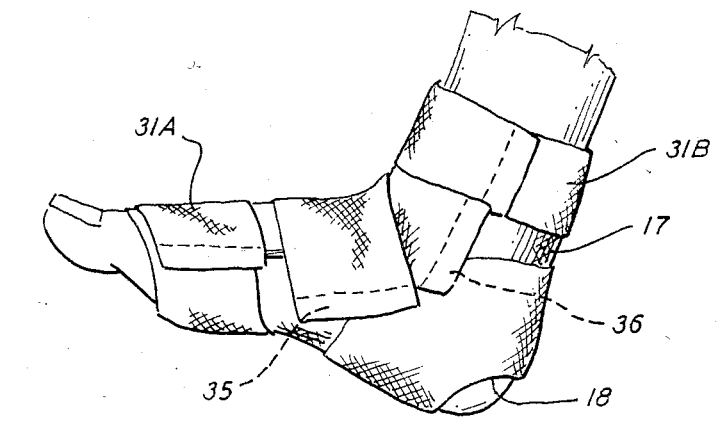
FIG. 12 illustrates the complete boot assembly with the ankle and toe straps and intermediate strap in place.

Next an intermediate strap 34 is applied which in flat form is of angled configuration as shown in FIG. 11. The intermediate 34 includes on one side thereof end hook-and-pile patches 35 and 36 and a central hook and-and-pile patch 37. In the example shown the central patch 37 is applied to the boot element at the inside of the patient's right heel. That end of the intermediate strap 34 with the patch 35 is then wrapped around the boot element from right-to-left as viewed by the patient, followed by a similar wrapping at the other end of the intermediate strap 34 so that when fully applied the intermediate strap 34 appears as shown in FIG. 12. Finally, another strap identical to that shown in FIG. 9 is applied about the top of the boot in the same manner as toe strap 31A. This ankle strap is designated 31B in FIG. 12.

It may be desirable to include a rigid plastic stirrup within the assembly if the sprain is particularly severe and joint restriction is necessary. Such stirrups consist of two upwardly extending legs which are arranged on either side of the patient's ankle and a connecting lower portion which is disposed beneath the sole of the foot. Such a stirrup would be applied directly over the boot element 17 and the toe and ankle straps 31A and 31B and the intermediate strap 34 would be wrapped around the stirrup.

The pad 12 may also be made of multi-ply foam construction with a relatively rigid central layer providing more support and relatively soft outer layers contacting the patient's skin. The pad may also include perspiration-absorbent exterior layers.

It will be evident from the foregoing description the boot assembly is completely reversible and eversible so that it can be applied either to the left or the right ankle and foot for an inversion or an everion sprain.

I claim:

1. A boot assembly applicable to either the left or right ankle and foot for applying compression to control edema from a sprain comprising
    (a) substantially U-shaped pad means of compressible material comprising two legs defining a channel and a connecting portion disposable on the foot with the malleolus between the legs at the bottom of the channel and with the connecting portion on the top of the foot below the malleolus;
    (b) a pliable fabric boot element disposable over the pad means around the ankle and foot from behind with a sole portion of the boot element underlying the foot and comprising
        i. upper and lower flaps on one side and upper and lower flaps on the other side of the front of the boot element,
        ii. one of the upper flaps being an inner flap disposable against the ankle and the other of the upper flaps being an outer flap adapted to overlap and be secured to the upper inner flap,
        iii. the lower flap on the same side as the upper outer flap being an inner flap disposable over the connecting portion of the pad means and the other of the lower flaps being an outer flap adapted to overlap and be secured to the lower inner flap in a direction opposite the overlap of the upper outer flap so as to compress the top of the boot and its area below the malleolus with a squeezing action opposed by the boot sole portion underlying the foot; and
    (c) releasable securing means on the upper and lower outer flaps for securing them to the respective upper and lower inner flaps.

2. A boot assembly according to claim 1 wherein the releasable securing means are on the inside of each of the upper and lower flaps.

3. A boot assembly according to claim 2 wherein each of said securing means is an infinitely adjustable quick-release hook-and-pile fastener patch.

4. A boot assembly according to claim 1 wherein the boot element has substantially identical inner and outer surfaces upon eversion and hence is reversible and eversible to fit either ankle and foot with a selected right-to-left or left-to-right direction of overlap of the flaps.

5. A boot assembly according to claim 1 wherein the inner flaps of the boot element are shorter than the corresponding outer flaps thereof.

6. A boot assembly according to claim 1 which includes elastic strap means for firmly and resiliently surrounding the boot element comprising
    (a) ankle and toe straps disposable respectively around the upper and lower portions of the boot element, and
    (b) an intermediate strap disposable about the boot element around the front of and behind the foot.

7. A boot assembly according to claim 6 wherein the ankle and toe straps are straight and the intermediate strap is angled.

8. A boot assembly according to claim 6 wherein the elastic strap means further includes infinitely adjustable quick-release hook-and-pile fastener means for connecting overlapping end portions of each of said straps.

9. A boot assembly according to claim 1 wherein removable attachment means are provided for holding the pad means to the inside of the boot element.

10. A boot assembly according to claim 1 which further includes a rigid stirrup comprising two upwardly extending legs adapted to be disposed on either side of the patient's ankle and a connecting lower portion adapted to be disposed beneath the sole of the patient's foot.

11. A boot assembly applicable to either the left or right ankle and foot for applying compression to control edema from a sprain comprising
    (a) substantially U-shaped pad means of compressible material comprising two legs defining a channel and a connecting portion disposable on the foot with the malleolus between the legs at the bottom of the channel and with the connecting portion on the top of the foot below the malleolus;
    (b) the legs of the pad means being initially nonparallel and closer at their outer ends when the pad means is flat and which assume a substantially parallel position when conformed to a patient's foot and ankle;
    (c) a pliable fabric boot element disposable over the pad means around the ankle and foot from behind with a sole portion of the boot element underlying the foot comprising
        i. upper and lower flaps on one side and upper and lower flaps on the other side of the front of the boot element,
        ii. one of the upper flaps being an inner flap disposable against the ankle and the other of the upper flaps being an outer flap adapted to overlap and be secured to the upper inner flap, iii. the lower flap on the same side as the upper outer flap being an inner flap disposable over the connecting portion of the pad means and the other of the lower flaps being an outer flap adapted to overlap and be secured to the lower inner flap in a direction opposite the overlap of the upper outer flap so as to compress the top of the foot and its area below the malleolus with a squeezing action opposed by the boot sole portion underlying the foot;

(d) ankle and toe straps disposable respectively around upper and lower portions of the boot element;

(e) an intermediate strap disposable about the boot element around the front of and behind the foot;

(f) releasable securing means on the inside of the upper and lower outer flaps for securing them to the respective upper and lower inner flaps; and (g) a rigid stirrup comprising two upwardly extenidng legs adapted to be disposed on either side of the patient's ankle and a connecting lower portion adapted to be disposed beneath the sole of the patient's foot.

12. A boot assembly applicable to either the left or right ankle and foot for applying compression to control edema from either an inversion or an eversion sprain comprising (a) a pliable fabric boot element disposable around the ankle and foot from behind and comprising
 i. upper and lower flaps on one side and upper and lower flaps on the other side of the front of the boot element,
 ii. one of the upper flaps being an inner flap disposable against the ankle and the other of the upper flaps being an outer flap adapted to overlap and be secured to the upper inner flap,
 iii. the lower flap on the same side as the upper outer flap being an inner flap disposable against the foot and the other of the lower flaps being an outer flap adapted to overlap and be secured to the lower inner flap in a direction opposite the overlap of the upper outer flap,
 iv. whereby the boot element is reversible and eversible to fit either ankle and foot with a selected right-to-left or left-to-right direction of overlap of the flaps; and (b) pad means adapted to be compressed around the malleolus within the boot element comprising a substantially U-shaped element which includes two legs; and (c) removable attachment means for holding the pad means to the inside of the boot element and wherein the removable attachment means are hook-and-pile patches attachable to the respective legs.

* * * * *